US012697347B2

(12) United States Patent
Dao et al.

(10) Patent No.: US 12,697,347 B2
(45) Date of Patent: Aug. 4, 2026

(54) PHARMACEUTICAL COMPOSITIONS AND METHODS OF USING THE SAME FOR TREATING CANCER

(71) Applicant: Taiho Pharmaceutical Co., Ltd., Tokyo (JP)

(72) Inventors: Kim-Hien Dao, Pleasanton, CA (US); Harold Keer, Pleasanton, CA (US); Aram Oganesian, Pleasanton, CA (US)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 409 days.

(21) Appl. No.: 18/250,674

(22) PCT Filed: Oct. 27, 2021

(86) PCT No.: PCT/US2021/056809

§ 371 (c)(1),
(2) Date: Apr. 26, 2023

(87) PCT Pub. No.: WO2022/093930

PCT Pub. Date: May 5, 2022

(65) Prior Publication Data

US 2023/0405037 A1 Dec. 21, 2023

Related U.S. Application Data

(60) Provisional application No. 63/107,010, filed on Oct. 29, 2020.

(51) Int. Cl.

*A61K 31/7068* (2006.01)
*A61K 9/00* (2006.01)
*A61K 31/635* (2006.01)
*A61K 31/706* (2006.01)
*A61P 35/02* (2006.01)

(52) U.S. Cl.

CPC ........ *A61K 31/7068* (2013.01); *A61K 9/0053* (2013.01); *A61K 31/635* (2013.01); *A61K 31/706* (2013.01); *A61P 35/02* (2018.01)

(58) Field of Classification Search

None
See application file for complete search history.

(56) References Cited

U.S. PATENT DOCUMENTS

| | | | |
|---|---|---|---|
| 2015/0250775 A1 | 9/2015 | Michelson |
| 2017/0321284 A1 | 11/2017 | Mccarroll et al. |
| 2020/0085848 A1 | 3/2020 | Keer et al. |
| 2022/0110958 A1 | 4/2022 | Keer et al. |
| 2022/0387384 A1 | 12/2022 | Hitotsumachi et al. |

FOREIGN PATENT DOCUMENTS

| | | |
|---|---|---|
| WO | 2015066162 A1 | 5/2015 |
| WO | 2020196665 A1 | 10/2020 |
| WO | 2021113688 A1 | 6/2021 |
| WO | 2021144657 A1 | 7/2021 |
| WO | 2021173598 A1 | 9/2021 |
| WO | 2022093930 A1 | 5/2022 |
| WO | 2022251677 A1 | 12/2022 |
| WO | 2023049731 A2 | 3/2023 |

OTHER PUBLICATIONS

Ball BJ, Famulare CA, Stein EM, Tallman MS, Derkach A, Roshal M, Gill SI, Manning BM, Koprivnikar J, McCloskey J, Testi R. Venetoclax and hypomethylating agents (HMAs) induce high response rates in MDS, including patients after HMA therapy failure. Blood advances. Jul. 14, 2020;4(13):2866-70.*

Garcia-Manero G, Griffiths EA, Steensma DP, Roboz GJ, Wells R, McCloskey J, Odenike O, DeZern AE, Yee K, Busque L, O'Connell C. Oral cedazuridine/decitabine for MDS and CMML: a phase 2 pharmacokinetic/pharmacodynamic randomized crossover study. Blood, The Journal of the American Society of Hematology. Aug. 6, 2020;1.*

"Extended European Search Report corresponding to European Application No. 21887422.0 dated Jun. 12, 2024".

Garcia-Manero, Guillermo , et al., "Oral cedazuridine/ decitabine for MDS and CMML: a phase 2 pharmacokinetic/pharmacodynamic randomized crossover study", Blood 136(6):674-683 (Aug. 6, 2020).

Gu, Xiaorong , et al., "Decitabine- and 5-azacytidine resistance emerges from adaptive responses of the pyrimidine metabolism network", Leukemia 35:1023-1036 (2021).

Jonas, Brian A, et al., "How we use venetoclax with hypomethylating agents for the treatment of newly diagnosed patients with acute myeloid leukemia", Leukemia 33:2795-2804 (Oct. 18, 2019).

"International Preliminary Report on Patentability corresponding to International Application No. PCT/US2021/056809 mailed May 11, 2023".

"Declaration of Nipun Davar Ph.D. dated Dec. 15, 2023".

"Office Action corresponding to Israel Patent Application No. 294288 dated Apr. 22, 2025".

"Office Action corresponding to Japanese Patent Application No. 2022-550210 dated Mar. 27, 2025".

"Office Action corresponding to Mexican Patent Application No. MX/a/2021/004013 dated Apr. 4, 2025".

"Study of ASTX727 vs IV Decitabine in Participants With MDS, CMML, and AML", Clinical trial NCT03306264 https://clinicaltrials.gov/study/NCT03306264?tab=history&a=2#version-content-panel (Aug. 27, 2024) 24 pages.

(Continued)

*Primary Examiner* — Patrick T Lewis
(74) *Attorney, Agent, or Firm* — Myers Bigel, P.A.

(57) ABSTRACT

Provided according to embodiments of the invention are methods of treating a disorder in a subject in need thereof that include administering to the subject an effective amount of cedazuridine, an effective amount of decitabine, and an effective amount of venetoclax, thereby treating the disorder in the subject. In some embodiments of the invention, the disorder is a hyperproliferative disorder such as a cancer. In some embodiments, the disorder is a hematological cancer such as myelodysplastic syndromes (MDS), myeloproliferative neoplasms (MPN), leukemia (e.g., acute myeloid leukemia), or lymphoma.

16 Claims, No Drawings

(56) References Cited

OTHER PUBLICATIONS

Belali, et al., "Isolation Published and Characterization of Microcrystalline Cellulose Derived from Plants as on Excipient in Tablet : A Review", Indonesian Journal of Pharmaceutics 1(2):55-61 (Jun. 13, 2019).
Ferraris, et al., "Design, Synthesis, and Pharmacological Evaluation of Fluorinated Tetrahydrouridine Derivatives as Inhibitors of Cytidine Deaminase", Journal of Medicinal Chemistry 57(6):2582-2588 (Feb. 12, 2014).
Garcia-Manero, et al., "Pharmacokinetic exposure equivalence and preliminary efficacy and safety from a randomized cross over phase 3 study (Ascertain study) of an oral hypomethylating agent A5TX727 (cedazuridine/decitabine) compared to IV decitabine", Blood 134:846 (Nov. 13, 2019).
Garcia-Manero, et al., "Pharmacokinetic Exposure Equivalence and Preliminary Efficacy and Safety from a Randomized Cross over Phase 3 Study (Ascertain study) of an Oral Hypomethylating Agent ASTX727 (cedazuridine/decitabine) Compared to IV Decitabine", Presentation, 61st ASH Annual Meeting Abstract 846 (Dec. 10, 2019) 15 pages.
Roboz, et al., "All-oral decitabine-cedazuridine (DEC-C) + venetoclax (VEN) in patients with newly diagnosed acute myeloid leukemia (AML) ineligible for induction chemotherapy: Phase 1/2 clinical trial results", EHA Congress (Jun. 12-15, 2025) 24 pages.
Rogstad, et al., "Chemical decomposition of 5-aza-2'-deoxycytidine on (Decitabine): kinetic analyses and identification of products by NMR, HPLC, and mass spectrometry", Chem. Res. Toxicol. 22(6):1194-1204 (Jun. 2009).
Savona, et al., "An Oral Fixed-Dose Combination of Decitabine and Cedazuridine in Myelodysplastic 1-4 Syndromes: a Multicentre, Open-Label, Dose-Escalation, Phase I Study", Lancet Haematol. 6(4):e194-e203 (Apr. 2019).
Thoorens, et al., "Microcrystalline cellulose, a direct compression binder in a quality by design environment—A review", International Journal of Pharmaceutics 473:64-72 (Jun. 30, 2014).
"Abbvie. "Prescribing Information"", Genentech USA, Inc. A Member of the Roche Group (May 2019) 49 pages.
"International Search Report and Written Opinion corresponding to International Application No. PCT/US2021/056809 mailed Feb. 1, 2022".
"Extended European Search Report corresponding to European Application No. 22873816.7 dated Jun. 30, 2025".
"Office Action corresponding to Australian Application No. 2021369508 dated Aug. 26, 2025".
"Office Action corresponding to Taiwanese Application No. 110139922 dated Jul. 16, 2025".
Chan, et al., "Chronic myelomonocytic leukemia diagnosis and management", Leukemia 35(6):1552-1562 (Mar. 13, 2021).
Garcia-Manero, et al., "Efficacy and safety of extended dosing schedules of CC-486 (oral azacitidine) in patients with lower-risk myelodysplastic syndromes", Leukemia 30(4):889-896 (Feb. 5, 2016).
Ravandi, Farhad , et al., "Phase 2 study of ASTX727 (cedazuridine/decitabine) plus venetoclax (ven) in patients with relapsed/refractory acute myeloid leukemia (AML) or previously untreated, elderly patients (pts) unfit for chemotherapy", Journal of Clinical Oncology 40(16):https://doi.org/10.1200/JCO.2022.40.16_suppl.7037 (Abstract Only) 3 pages (Jun. 2, 2022).
U.S. Appl. No. 18/304,396; office action mailed Sep. 25, 2025.
International Preliminary Report on Patentability corresponding to International Application No. PCT/US2024/027160 mailed Nov. 13, 2025.
International Search Report and Written Opinion corresponding to International Application No. PCT/US2024/027160 mailed Aug. 8, 2024.
Office Action corresponding to Australian Application No. 2020363412 dated Jul. 15, 2025.
Office Action corresponding to Philippines Application No. 12022550795 dated Oct. 6, 2025.
Garcia-Manero, et al., "Successful Emulation of IV Decitabine Pharmacokinetics with an Oral Fixed-Dose Combination of the Oral Cytidine Deaminase Inhibitor (CDAi) E7727 with Oral Decitabine, in Subjects with Myelodysplastic Syndromes (MDS): Final Data of Phase 1 Study", Blood, 128(22):114, 2016, (4 pp).
Nakatsuji, et al., "Theoretical study on the catalytic activity of palladium for the hydrogenation of acetylene", Surface Science, 185(1-2), 1987, 319-342.
Roboz, et al., "All-oral decitabine-cedazuridine (DEC-C) + venetoclax (VEN) in patients with newly diagnosed acute myeloid leukemia (AML) ineligible for induction chemotherapy: Phase 1/2 clinical trial results", Abstract of Oral Presentation + PPT Presentation, presented on Jun. 12, 2025, at EHA 2025 Congress Jun. 12-15, 2025, Milan, Italy, (24 pp).
Sharma, et al., "Clinical Outcomes Associated with Drug-Drug Interactions of Oral Chemotherapeutic Agents: A Comprehensive Evidence-Based Literature Review", Drugs & Aging, 36(4), 2019, 341-354.
Taiho Oncology, "Taiho Oncology, Inc. & Taiho Pharmaceutical Co., Ltd., Taiho Oncology and Taiho Pharmaceutical Announce U.S. FDA Acceptance of Supplemental New Drug Application for Inqovi® in Combination with Venetoclax to Treat Patients with Acute Myeloid Leukemia", (Jul. 9, 2025), available at https://www.taihooncology.com/us/news/taiho-oncology-and-taiho-pharmaceutical-announce-us-fda-acceptance-of-supplemental-new-drug-application-for-inqovi-in-combination-with-venetoclax-to-treat-patients-with-acute-myeloid-leukemia/, (6 pp).
"Office Action corresponding to Japanese Patent Application No. 2023-526030 issued Jan. 20, 2026".
"Examination Report corresponding to European Application No. 21887422.0 dated Feb. 11, 2026".
Aduma, et al., "Anti-herpes virus activity of 5-methoxymethyl-2'-deoxycytidine in combination with deaminase inhibitors", Antiviral Chemistry & Chemotherapy 1(4):255-262 (1990).
Bazinet, et al., "833 A Phase 2 Study of the Fully Oral Combination of ASTX727 (Decitabine/Cedazuridine) Plus Venetoclax for Older and/or Unfit Patients with Acute Myeloid Leukemia", Program: Oral and Poster Abstracts (Dec. 11, 2023) https://ash.confex.com/ash/2023/wcbprogram/Paper172658.html (4 pages).
Bouffard, et al., "Kinetic Studies on 2',2'-Difluorodeoxycytidine (Gemcitabine) With Purified Human Deoxycytidine Kinase and Cytidine Deaminase", Biochemical Pharmacology 45(9):1857-1861 (Jan. 8, 1993).
Cacciamani, et al., "Purification of Human Cytidine Deaminase: Molecular and Enzymatic Characterization and Inhibition by Synthetic Pyrimidine Analogs", Arch. Biochem. Biophys. 290(2):285-292 (Nov. 1, 1991).
Eliopoulos, et al., "Drug resistance to 5-aza-2'-deoxycytidine, 2',2'-difluorodeoxycytidine, and cytosine arabinoside conferred by retroviral-mediated transfer of human cytidine deaminase cDNA into murine cells", Cancer Chemother Pharmacol 42:373-378 (Jan. 16, 1998).
Garciaz, et al., "Azacitidine Plus Venetoclax for the Treatment of Relapsed and Newly Diagnosed Acute Myeloid Leukemia Patients", Cancers 14(8):2025 (Apr. 16, 2022).
Kees, et al., "Development of Resistance to 1-beta-D-Arabinofuranosylcytosine after High-Dose Treatment in Childhood Lymphoblastic Leukemia: Analysis of Resistance Mechanism in Established Cell Lines", Cancer Research 49:3015-3019 (Jun. 1, 1989).
Konopleva, et al., "Efficacy and Biological Correlates of Response in a Phase II Study of Venetoclax Monotherapy in Patients with Acute Myelogenous Leukemia", Cancer Discovery 6(10):1106-1117 (Oct. 2016).
Momparler, et al., "Induction of Cytidine Deaminase in HL-60 Myeloid Leukemic Cells by 5-AZA-2'-Deoxycytidine", Leukemia Research 14(9):751-754 (Mar. 10, 1990).
Wentworth, et al., "Cytidine Deaminases (from *Escherichia coli* and Human Liver)", Methods Enzymol. 51:401-407 (1978).
Wisdom, et al., "Cytidine Aminohydrolase from Sheep Liver", Biochem. J. 104:7p (1967) 1 page.

(56) References Cited

OTHER PUBLICATIONS

"Office Action corresponding to Israeli Application No. 294288 dated Mar. 22, 2026".
"Office Action corresponding to Vietnamese Application No. 1-2022-05796 dated Mar. 27, 2026".
"INQOVI® (decitabine and cedazuridine) tablets, for oral use Initia U.S. Approval", https://www.accessdata.fda.gov/drugsatfda_doc/label/2020/212576s000lbl.pdf (2020) 24 pages.

* cited by examiner

PHARMACEUTICAL COMPOSITIONS AND METHODS OF USING THE SAME FOR TREATING CANCER

STATEMENT OF PRIORITY

This application is a 35 U.S.C. § 371 national phase application of PCT Application PCT/US2021/056809 filed Oct. 27, 2021, which claims the benefit of U.S. Provisional Application Ser. No. 63/107,010, filed Oct. 29, 2020, the entire contents of each of which are incorporated by reference herein.

FIELD OF THE INVENTION

The present invention relates to pharmaceutical compositions and methods for the treatment of cancers such as leukemia.

BACKGROUND OF THE INVENTION

Decitabine (5-aza-2'-deoxycytidine), a cytidine analog, is an antineoplastic agent and hypomethylating agent (HMA) for the treatment of myelodysplastic syndrome (MDS), with potential utility for the treatment of acute myeloid leukemia (AML) and chronic myelomonocytic leukemia (CMML) as well.

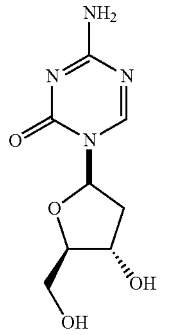

5-aza-2′-deoxycytidine
(decitabine)

Cedazuridine ((4R)-2'-deoxy-2'2'-difluoro-3,4,5,6-tetrahydrouridine; also known as E7727) is a CDA inhibitor. Cedazuridine and methods of making and/or using the same are further disclosed in U.S. Pat. Nos. 8,268,800 and 9,834,576, the contents of each of which are incorporated by reference herein in their entirety.

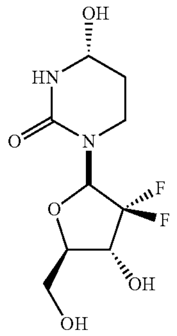

Cedazuridine

Astex Pharmaceuticals, Inc. received FDA approval for a fixed dose combination of decitabine and cedazuridine which is sold under the brand name INQOVI® by Taiho Oncology, Inc.

Venetoclax (4-[4-[[2-(4-chlorophenyl)-4,4-dimethylcyclohexen-1-yl]methyl]piperazin-1-yl]-N-[3-nitro-4-(oxan-4-ylmethylamino)phenyl]sulfonyl-2-(1H-pyrrolo[2,3-b]pyridin-5-yloxy)benzamide; CAS 1257044-40-8) is a BH3-memetic that has been shown to block the B-cell lymphoma-2 (Bcl-2) protein. Venetoclax has been used to treat chronic lymphocytic leukemia (CLL), small lymphocytic lymphoma (SLL), and acute myeloid leukemia (AML) in adults.

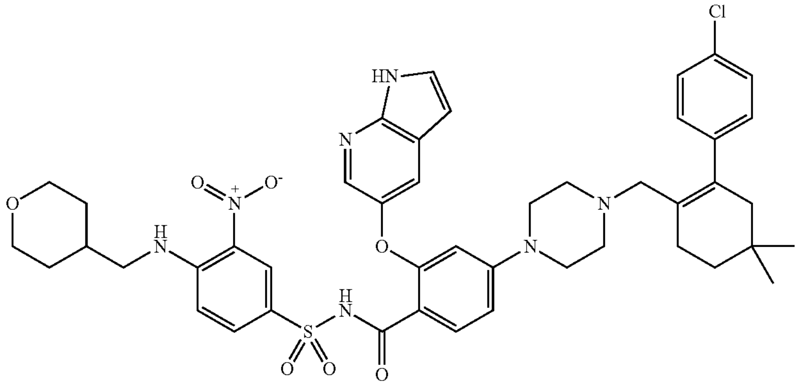

Venetoclax

While the use of a combination of active pharmaceutical agents may provide beneficial therapeutic effects to patients, there may also be drug-drug interactions that alter the pharmacokinetic effects of the active pharmaceutical agents, or are toxic or otherwise harmful to the patient.

Summary of Embodiments of the Invention

Provided according to embodiments of the invention are methods of treating a disorder in a subject in need thereof that include administering to the subject an effective amount of cedazuridine, an effective amount of decitabine, and an effective amount of venetoclax, thereby treating the disorder in the subject. In some embodiments of the invention, the disorder is a hyperproliferative disorder such as a cancer. In some embodiments, the disorder is a hematological cancer such as myelodysplastic syndromes (MDS), myeloproliferative neoplasms (MPN), leukemia (e.g., acute myeloid leukemia), or lymphoma. In some embodiments, the subject is aged 75 years or older and/or has one or more comorbidities that preclude the use of standard induction chemotherapy.

In some embodiments of the invention, the effective amount of cedazuridine, the effective amount of decitabine, and the effective amount of venetoclax are administered as a solid oral dosage form. In some embodiments, the effective amount of cedazuridine and the effective amount of decitabine are administered together in a combination solid oral dosage form. In some embodiments, the effective amount of cedazuridine and the effective amount of decitabine are administered on days 1-5 of a 28-day cycle, and the effective amount of venetoclax is administered each day of the 28-day cycle.

Also provided according to embodiments of the invention is a solid oral dosage form that includes cedazuridine, decitabine, and venetoclax, and at least one pharmaceutically acceptable excipient.

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of skill in the art to which this invention belongs. The terminology used in the description of the invention herein is for the purpose of describing particular embodiments only and is not intended to be limiting of the invention.

All publications, patent applications, patents, nucleotide sequences, amino acid sequences and other references mentioned herein are incorporated by reference in their entirety.

Definitions

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

Moreover, the present invention also contemplates that in some embodiments of the invention, any feature or combination of features set forth herein can be excluded or omitted.

Furthermore, the term "about," as used herein when referring to a measurable value such as an amount of a compound or agent of this invention, dose, time, temperature, and the like, is meant to encompass variations of ±10%, ±5%, ±1%, ±0.5%, or even±0.1% of the specified amount.

As used herein, the transitional phrase "consisting essentially of" is to be interpreted as encompassing the recited materials or steps and those that do not materially affect the basic and novel characteristic(s) of the claimed invention. Thus, the term "consisting essentially of" as used herein should not be interpreted as equivalent to "comprising."

"Effective amount" refers to the amount required to produce a desired effect (e.g., enhancing the half-life, bioavailability or efficacy of a therapeutic agent treating cancer in a subject, or reducing DNA methylation in a subject).

"Pharmaceutically acceptable" refers to those properties and/or substances that are acceptable to the patient from a pharmacological and/or toxicological point of view, and/or to the manufacturing pharmaceutical chemist from a physical and/or chemical point of view regarding composition, formulation, stability, patient acceptance, bioavailability and compatibility with other ingredients.

"Pharmaceutically acceptable salt" refers to an acid or base salt of a compound of the invention, which salt possesses the desired pharmacological activity and is neither biologically nor otherwise undesirable. The salt can be formed with acids that include without limitation acetate, adipate, alginate, aspartate, benzoate, benzenesulfonate, bisulfate butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride hydrobromide, hydroiodide, 2-hydroxyethane-sulfonate, lactate, maleate, methanesulfonate, 2-naphthalenesulfonate, nicotinate, oxalate, thiocyanate, tosylate and undecanoate. Examples of a base salt include without limitation ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine. In some embodiments, the basic nitrogen-containing groups can be quaternized with agents including lower alkyl halides such as methyl, ethyl, propyl and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; and aralkyl halides such as phenethyl bromides.

"Pharmaceutically acceptable excipient" can mean any substance, not itself a therapeutic agent, used as a carrier, diluent, adjuvant, binder, and/or vehicle for delivery of a therapeutic agent to a subject, or added to a pharmaceutical composition to improve its handling or storage properties or to permit or facilitate formation of a compound or composition into a unit dosage form for administration.

"Unit dosage form" refers to a physically discrete unit suitable as a unitary dosage for human or other animal subjects. Each unit dosage form may contain a predetermined amount of an active substance (e.g., cedazuridine, decitabine and/or venetoclax) calculated to produce a desired effect.

"Optional" or "optionally" means that the subsequently described event or circumstance may or may not occur, and that the description includes instances where the event or circumstance occurs and instances in which it does not. For example, an alkyl that is "optionally substituted" encompasses both an alkyl that is unsubstituted and an alkyl that is substituted.

The term "enhance" or "increase" refers to an increase in the specified parameter of at least about 1.25-fold, 1.5-fold, 2-fold, 3-fold, 4-fold, 5-fold, 6-fold, 8-fold, 10-fold, twelve-fold, fifteen-fold, etc.

The term "inhibit" or "reduce" or grammatical variations thereof, as used herein, refers to a decrease or diminishment in the specified level or activity of at least about 15%, 25%, 35%, 40%, 50%, 60%, 75%, 80%, 90%, 95% or more. In particular embodiments, the inhibition or reduction results in little or essentially no detectible activity (at most, an insignificant amount, e.g., less than about 10% or even 5%).

"Subject" refers to a cell or tissue, in vitro or in vivo, an animal or a human. An animal or human subject may also be referred to as a "patient."

"Animal" refers to a living organism having sensation and the power of voluntary movement, and which requires for its existence oxygen and organic food.

"Mammal" refers to a warm-blooded vertebrate animal with hair or fur. Examples include without limitation members of the human, equine, porcine, bovine, murine, canine or feline species.

By the term "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved. "Treating" in reference to a disease, disorder or condition may refer to: (i) inhibiting a disease, disorder or condition, e.g., arresting its development, (ii) relieving a disease, disorder or condition, e.g., causing regression of the clinical symptoms; and/or (iii) stabilizing or controlling the progression of a disease, disorder or condition, including preventing a relapse or disease progression after a reduction in or absence of a detectable level of disease.

The term "administering" or "administration" of a compound and/or composition of the present invention to a subject includes a route of introducing or delivering to a subject a compound to perform its intended function.

"Cancer" refers to an abnormal growth of cells which tend to proliferate in an uncontrolled way and, in some cases, to metastasize (spread). Specific cancers types include without limitation the cancers identified in Publication No. US 2006/0014949 and the following: cardiac: sarcoma (e.g., such as angiosarcoma, fibrosarcoma, rhabdomyosarcoma, liposarcoma and the like), myxoma, rhabdomyoma, fibroma, lipoma and teratomas; lung: bronchogenic carcinoma (e.g., such as squamous cell, undifferentiated small cell, undifferentiated large cell, adenocarcinoma and the like), alveolar (e.g., such as bronchiolar), carcinoma, bronchial adenoma, sarcoma, lymphoma, chondromatous hamartoma, and mesothelioma; gastrointestinal: esophagus (e.g., such as squamous cell carcinoma, adenocarcinoma, leiomyosarcoma, lymphoma and the like), stomach (e.g., such as carcinoma, lymphoma, leiomyosarcoma and the like), pancreas (e.g., such as ductal adenocarcinoma, insulinoma, glucagonoma, gastrinoma, carcinoid tumors, vipoma and the like), small bowel (e.g., such as adenocarcinoma, lymphoma, carcinoid tumors, Kaposi's sarcoma, leiomyoma, hemangioma, lipoma, neurofibroma, fibroma, and the like), and large bowel (e.g., such as adenocarcinoma, tubular adenoma, villous adenoma, hamartoma, leiomyoma and the like); genitourinary tract: kidney (e.g., such as adenocarcinoma, Wilm's tumor nephroblastoma, lymphoma, leukemia, and the like), bladder and urethra (e.g., such as squamous cell carcinoma, transitional cell carcinoma, adenocarcinoma and the like), prostate (e.g., such as adenocarcinoma, sarcoma), and testis (e.g., such as seminoma, teratoma, embryonal carcinoma, teratocarcinoma, choriocarcinoma, sarcoma, interstitial cell carcinoma, fibroma, fibroadenoma, adenomatoid tumors, lipoma and the like); liver: hepatoma (e.g., hepatocellular carcinoma and the like), cholangiocarcinoma, hepatoblastoma, angiosarcoma, hepatocellular adenoma, and hemangioma; bone: osteogenic sarcoma (e.g., such as osteosarcoma and the like), fibrosarcoma, malignant fibrous histiocytoma, chondrosarcoma, Ewing's sarcoma, malignant lymphoma (e.g., such as reticulum cell sarcoma), multiple myeloma, malignant giant cell tumor chordoma, osteochondroma (e.g., such as osteocartilaginous exostoses), benign chondroma, chondroblastoma, chondromyxofibroma, osteoid osteoma and giant cell tumors; nervous system: skull (e.g., such as osteoma, hemangioma, granuloma, xanthoma, osteitis deformans and the like), meninges (e.g., such as meningioma, meningiosarcoma, gliomatosis and the like), brain (e.g., such as astrocytoma, medulloblastoma, glioma, ependymoma, germinoma [pinealoma], glioblastoma multiform, oligodendroglioma, schwannoma, retinoblastoma, congenital tumors and the like), and spinal cord (e.g., such as neurofibroma, meningioma, glioma, sarcoma and the like); gynecological: uterus (e.g., such as endometrial carcinoma and the like), cervix (e.g., such as cervical carcinoma, pre-tumor cervical dysplasia and the like), ovaries (e.g., such as ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma, and the like), vulva (e.g., such as squamous cell carcinoma, intraepithelial carcinoma, adenocarcinoma, fibrosarcoma, melanoma and the like), vagina (e.g., such as clear cell carcinoma, squamous cell carcinoma, botryoid sarcoma (embryonal rhabdomyosarcoma], fallopian tubes (carcinoma) and the like); hematologic: blood (e.g., such as myeloid leukemia [acute and chronic], acute lymphoblastic leukemia, chronic lymphocytic leukemia, myeloproliferative diseases, multiple myeloma, myelodysplastic syndrome and the like), Hodgkin's disease, and non-Hodgkin's lymphoma; skin: malignant melanoma, basal cell carcinoma, squamous cell carcinoma, Kaposi's sarcoma, moles dysplastic nevi, lipoma, angioma, dermatofibroma, keloids, psoriasis and the like; and adrenal glands: neuroblastoma.

"Complete Response" (CR), as used herein, refers to bone marrow blasts less than 5%; absence of circulating blasts and blasts with Auer rods; absence of extramedullary disease; absolute neutrophil count less than $1.0\times10^9$/L (1,000/μL); and platelet count less than $100\times10^9$/L (100,000/μL). This definition follows the European LeukemiaNet (ELN) 2017 classification for AML, and such standards may change upon further iterations by the ELN. Other diseases, including MDL/CMML, may have different response criteria based on ELN or other working group standards.

"Complete Response with incomplete blood count recovery" (CRi), as used herein, refers to all CR criteria except for residual neutropenia [less than $1.0\times10^9$/L (1,000/μL)] or thrombocytopenia [less than $100\times10^9$/L (100,000/μL)]. This definition follows the European LeukemiaNet (ELN) 2017 classification for AML, and such standards may change upon further iterations by the ELN. Other diseases, including MDL/CMML, may have different response criteria based on ELN or other working group standards.

"Complete Response with partial hematological recovery" (CRh), as used herein, refers to all CR criteria except not meeting count recovery criteria; and having an absolute neutrophil count of less than or equal to $0.5\times10^9$/L (1,000/μL) and platelet count of less than or equal to $50\times10^9$/L (100,000/μL). This is a current commonly used definition for AML. Other diseases, including MDL/CMML, may have different response criteria based on ELN or other working group standards.

"$AUC_{0-t}$" is the definite integral of a curve that describes the variation of drug concentration in blood plasma over time (t).

For decitabine "5-day cumulative AUC," the Primary Endpoint Pharmacokinetic (PK) Analysis Set is used to calculate 5-day cumulative $AUC_{0-t}$ exposures after administration of the dosage form. The following assumptions are used: 1) Steady state is reached on Day 2 of dosing with the solid dosage form; and 2) Based on steady state achievement on Day 2, $AUC_{0-t}$ from Day 2 and Day 5 is representative of daily $AUC_{0-t}$ on Days 2 through Day 5 in a putative 5-day dosing with the solid dosage form. Therefore, to calculate total decitabine 5-day oral $AUC_{0-t}$ exposures using PK data from 3 days of serial PK sampling, Day 1 $AUC_{0-t}$ (first solid dosage form dose) is added to (Day 2 $AUC_{0-t}$+Day 5 $AUC_{0-t}$)×2. If $AUC_{0-t}$ on Day 2 is not available, it is replaced by $AUC_{0-t}$ on Day 5; the converse is also true.

"Cmax" is the maximum (or peak) serum concentration that a drug achieves in the blood or other matrix after a drug has been administered and before administration of a second dose. As such, the Cmax may be determined on any day of the cycle.

A "cycle," as used herein, refers to 28 consecutive days wherein the cedazuridine, decitabine, and venetoclax are administered. In some embodiments, cedazuridine and decitabine are administered for days 1-5 of each 28-day cycle. In some embodiments, venetoclax is administered daily for the 28-day cycle. Multiple cycles may be performed, either consecutively, or with a break between cycles. Additionally, other cycle lengths and different dosing regimens could be used.

The present invention provides oral dosage forms for decitabine, cedazuridine, and venetoclax, or a pharmaceutically acceptable salt of any of the foregoing, wherein these three medicaments may be administered simultaneously, sequentially, or separately. As used herein, decitabine, cedazuridine, and venetoclax, and their pharmaceutically acceptable salts, may be referred to collectively as "therapeutic agents." Additionally, when a therapeutic agent (e.g., venetoclax) is referenced, it is to be understood that the therapeutic agent's pharmaceutically acceptable salts are also included in this reference. The oral dosage forms may include each therapeutic agent separately, all of the therapeutic agents in combination, or any two of the therapeutic agents in combination. In particular embodiments, a first oral dosage form comprises decitabine and cedazuridine, and a second oral dosage form comprises venetoclax. In particular embodiments, a solid oral dosage form comprises decitabine, cedazuridine, and ventoclax. In some embodiments, the solid oral dosage form of the invention further includes a pharmaceutically acceptable excipient.

In some embodiments of the invention, the one or more of the oral dosage forms is a solid oral dosage form, such as a solid oral unit dosage form. The term "solid oral dosage form" means that the pharmaceutical compositions are in solid form and are formulated for oral administration. Any suitable solid oral dosage form may be used. Examples of solid oral dosage forms according to embodiments of the invention include tablets (for example, those targeted for buccal, sublingual, or systemic absorption), caplets, boluses, powders, granules, pastes for application to the tongue, capsules including hard gelatin capsules and soft gelatin capsules, mouth sprays, troches, lozenges, and pellets. The pharmaceutical compositions may be formulated for immediate, sustained, or controlled release.

A number of possible oral dosage forms could be used in the methods of the invention. For example, decitabine may be present in an oral dosage form in a range of about 10 mg to about 100 mg, about 20 mg to about 45 mg, or about 30 mg to about 40 mg (e.g., about 10, 20, 25, 30, 35, 40, 45, 50, 55, 60, 65, 70, 75, 80, 90, or 100 mg, or any range therein). As another example, cedazuridine may be present in an oral dosage form in a range of about 10 mg to about 150 mg, about 70 mg to 120 mg, or about 90 mg to about 110 mg (e.g., about 50, 60, 70, 80, 85, 90, 95, 100, 105, 11, 115, 120, 125, 130, 140, or 150 mg, or any range therein). As yet another example, venetoclax may be present in the solid oral dosage form in a range of about 10 mg to about 600 mg, about 50 mg to about 400 mg, or about 50 mg to 200 mg (e.g., about 10, 20, 30, 40, 50, 60, 70, 80, 90, 100, 110, 120, 150, 200, 250, 300, 400, 450, 500, 550, 600 mg, or any range therein). However, in some embodiments of the invention, one solid oral dosage form is a unit dosage form that comprises about 35 mg decitabine. In some embodiments of the invention, one solid oral dosage form is unit dosage form that comprises about 100 mg of cedazuridine. Furthermore, in some embodiments, one solid oral dosage form is a unit dosage form that comprises about 35 mg decitabine and about 100 mg of cedazuridine. In some embodiments of the invention, one unit dosage form comprises about 35 mg decitabine and about 100 mg of cedazuridine and at least one pharmaceutically acceptable excipient. In some embodiments of the invention, one solid oral dosage form is a unit dosage form that comprises about 10 mg, 50 mg, 100 mg, 200 mg, 400 mg, or 600 mg venetoclax and at least one pharmaceutically acceptable excipient. In some embodiments of the invention, one solid oral dosage form is a unit dosage form that comprises about 35 mg decitabine, about 100 mg of cedazuridine, and about 10 mg, 50 mg, 100 mg, 200 mg, 400 mg, or 600 mg of venetoclax. In some embodiments of the invention, one solid oral dosage form is a unit dosage form that comprises about 35 mg decitabine, about 100 mg of cedazuridine, about 10 mg, 50 mg, 100 mg, 200 mg, 400 mg, or 600 mg of venetoclax, and at least one pharmaceutically acceptable excipient.

Pharmaceutically acceptable excipients are well known in the pharmaceutical arts and are described, for example, in Remington's Pharmaceutical Sciences, Mack Publishing Co., Easton, Pa (e.g., 20th Ed., 2000), and Handbook of Pharmaceutical Excipients, American Pharmaceutical Association, Washington, D.C., (e.g., 1st, 2nd and 3rd Eds., 1986, 1994 and 2000, respectively). As will be known to those skilled in the art, excipients may provide a variety of functions and may be described as, e.g., wetting agents, buffering agents, suspending agents, diluents, binders, lubricating agents, glidants, emulsifiers, disintegrants, absorbents, preservatives, surfactants, colorants, flavorants, and/or sweeteners. Examples of pharmaceutically acceptable excipients include without limitation: (1) sugars, such as lactose, glucose and sucrose; (2) starches, such as corn starch and potato starch; (3) cellulose and its derivatives, such as sodium carboxymethyl cellulose, ethyl cellulose, cellulose acetate, hydroxypropylmethylcellulose (hypromellose), and hydroxypropylcellulose; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Examples of diluents include lactose, lactose monohydrate, cellulose, microcrystalline cellulose, sorbitol, dibasic calcium phosphate dehydrate, and calcium sulfate dehydrate. Examples of binders include gelatin, glucose, lactose, cellulose, methyl cellulose, ethyl cellulose, hydroxypropyl methyl cellulose (hypromellose), hydroxypropyl cellulose, starch, poly vinyl pyrrolidone, sodium alginate, carboxymethylcellulose, and acacia. Examples of disintegrants include croscarmellose sodium, crospovidone, sodium starch glycollate, and starch. Examples of glidants include colloidal silicon dioxide, cornstarch and talc. Examples of lubricants include stearic acid, magnesium stearate, calcium stearate, talc, paraffin, sodium lauryl sulphate, sodium benzoate, and polyethylene glycol.

In some embodiments, a solid oral dosage form includes one or more of a diluent, binder, disintegrant, glidant, and lubricant. In some embodiments, a solid oral dosage form includes a diluent, binder, disintegrant, glidant, and lubricant. In particular embodiments of the invention, the solid oral dosage form includes decitabine and/or cedazuridine and the following excipients: lactose monohydrate as a diluent; hydroxypropyl methylcellulose as a binder; croscarmellose sodium as a disintegrant; colloidal silicon dioxide as a glidant; and magnesium stearate as a lubricant. In some embodiments of the invention, such components are formed into a tablet. In some embodiments, the tablet is an immediate release tablet. Additionally, in particular embodiments, the tablet is coated with a film, which may or may not be colored. Any pharmaceutically acceptable coating may be used but, in some embodiments, the tablet is coated with an Opadry© coating.

In some embodiments, cedazuridine is present in a solid oral dosage form in an amount of about 17-22% w/w, e.g., about 17.0, 17.2, 17.4, 17.6, 17.8, 18.0, 18.2, 18.4, 18.6, 18.8, 19.0, 19.2, 19.4, 19.6, 19.8, 20.0, 20.2, 20.4, 20.6, 20.8, 21.0, 21.2, 21.4, 21.6, 21.8, or 22.0% w/w or any range therein, e.g., about 19.42% w/w. In some embodiments, decitabine is present in the solid oral dosage form in an amount of about 4-8% w/w, e.g., about 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, or 8.0% w/w or any range therein, e.g., about 6.8% w/w. In some embodiments, the diluent (e.g., lactose monohydrate) is present in the solid oral dosage form in an amount of about 55-70% w/w, e.g., about 55, 56, 57, 58, 59, 60, 61, 62, 63, 64, 65, 66, 67, 68, 69, or 70% w/w or any range therein, e.g., about 62.62% w/w. In some embodiments, the binder (e.g., hypromellose) is present in the solid oral dosage form in an amount of about 1-3% w/w, e.g., about 1.0, 1.2, 1.4, 1.6, 1.8, 2.0, 2.2, 2.4, 2.6, 2.8, or 3.0% w/w or any range therein, e.g., about 1.94% w/w. In some embodiments, the disintegrant (e.g., croscarmellose sodium) is present in the solid oral dosage form in an amount of about 3-7% w/w, e.g., about 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, or 7.0% w/w or any range therein, e.g., about 4.85% w/w. In some embodiments, the glidant (e.g., colloidal silicon dioxide) is present in the solid oral dosage form in an amount of about 0.5-2% w/w, e.g., about 0.5, 0.6, 0.7, 0.8, 0.9, 1.0. 1.1, 1.2, 1.3, 1.4, 1.5, 1.6, 1.7, 1.8, 1.9, or 2.0% w/w or any range therein, e.g., about 0.97% w/w. In some embodiments, the lubricant (e.g., magnesium stearate) is present in the solid oral dosage form in an amount of about 0.1-2% w/w, e.g., about 0.1, 0.2, 0.3, 0.4, 0.5, 0.6, 0.7, 0.8, 0.9, 1.0. 1.1, 1.2, 1.3, 1.4, 1.5, 1.6, 1.7, 1.8, 1.9, or 2.0% w/w or any range therein, e.g., about 0.49% w/w.

In some embodiments, the solid oral dosage form comprises the components listed in Table 1.

TABLE 1

| Component | Function | Composition (% w/w) |
|---|---|---|
| Cedazuridine | Active | 17-22 |
| Decitabine | Active | 4-8 |
| Lactose monohydrate | Diluent | 55-70 |
| Hypromellose | Binder | 1-3 |
| Croscarmellose sodium | Disintegrant | 3-7 |
| Colloidal silicon dioxide | Glidant | 0.5-2 |
| Magnesium stearate | Lubricant | 0.1-2 |

In some embodiments, the solid oral dosage form comprises the components listed in Table 2.

TABLE 2

| Component | Function | Composition (% w/w) |
|---|---|---|
| Cedazuridine | Active | 19.42 |
| Decitabine | Active | 6.80 |
| Lactose monohydrate | Diluent | 62.62 |
| Hypromellose | Binder | 1.94 |
| Croscarmellose sodium | Disintegrant | 4.85 |
| Colloidal silicon dioxide | Glidant | 0.97 |
| Magnesium stearate | Lubricant | 0.49 |
| Total Core Tablet | | 97.09 |
| Coating | Film Coat | 2.91 |
| Total Coated Tablet | | 100.0 |

More information regarding compositions and formulations for cedazuridine and decitabine may be found in the Inqovi® prescribing information and at www.inqovi.com.

In some embodiments of the invention, venetoclax is present in a solid oral dosage form (e.g., a tablet) at a concentration of 10 mg of venetoclax with one or more of the following excipients: calcium phosphate dibasic, colloidal silicon dioxide, copovidone, iron oxide yellow, polyethylene glycol, polysorbate 80, polyvinyl alcohol, sodium stearyl fumarate, talc and titanium dioxide.

In some embodiments of the invention, venetoclax is present in a solid oral dosage form (e.g., a tablet) at a concentration of 50 mg of venetoclax with one or more of the following excipients: calcium phosphate dibasic, colloidal silicon dioxide, copovidone, iron oxide black, iron oxide red, iron oxide yellow, polyethylene glycol, polysorbate 80, polyvinyl alcohol, sodium stearyl fumarate, talc, and titanium dioxide.

In some embodiment of the invention, venetoclax is present in a solid oral dosage form (e.g., a tablet) at a concentration of 100 mg of venetoclax with one or more of the following excipients: calcium phosphate dibasic, colloidal silicon dioxide, copovidone, iron oxide yellow, polyethylene glycol, polysorbate 80, polyvinyl alcohol, sodium stearyl fumarate, talc and titanium dioxide.

Pharmaceutical compositions of the invention can be prepared using known materials and techniques, which may include, but are not limited to, mixing and/or blending decitabine and cedazuridine with the pharmaceutically acceptable excipients. Pharmaceutical compositions of the invention may also include mixing and/or blending venetoclax with pharmaceutically acceptable excipients.

Another aspect of the present invention relates to a unit dosage form and a kit comprising at least one unit dosage form comprising decitabine, at least one unit dosage form comprising cedazuridine, and at least one unit dosage form comprising venetoclax. In particular embodiments, a kit comprises at least one unit dosage form comprising decitabine and cedazuridine and at least one unit dosage form comprising venetoclax. In some embodiments, the kit provides one unit dosage form that includes about 35 mg decitabine and about 100 mg of cedazuridine and at least one pharmaceutically acceptable excipient, and at least one unit dosage form that include about 10 mg, 50 mg, and/or 100 mg of venetoclax. Other unit dosage forms may be used and may vary depending on availability. The daily dose for cedazuridine, decitabine, and/or venetoclax may require more than one unit dosage form per day. For example, if 400 mg of venetoclax is prescribed per day, the kit may include four 100 mg venetoclax unit dosage forms for one day.

A kit may include the solid oral dosage forms for one day's dose of each therapeutic agent (e.g., one tablet comprising 35 mg decitabine and 100 mg cedazuridine, and four tablets comprising 100 mg venetoclax each). A kit may also include unit dosage forms for more than one day of the cycle (e.g., 5 days or a week) or for the full cycle. As such, in some embodiments of the invention, a kit may include 1, 2, 3, 4, 5, 6, 7, 8, 9, 10, 11, 12, 13, 14, 15, 16, 17, 18, 19, 20, 21, 22, 23, 24, 25, 26, 27, 28 or more solid oral dosage forms comprising cedazuridine and decitabine according to an embodiments of the invention, and 1, 2, 3, 4, 5, 6, 7, 8, 9, 10, 11, 12, 13, 14, 15, 16, 17, 18, 19, 20, 21, 22, 23, 24, 25, 26, 27, 28 or more solid oral dosage forms comprising venetoclax. In some embodiments, a kit may include 5 solid oral dosage forms comprising cedazuridine and decitabine (for days 1-5 of the cycle) and at least 28 solid oral dosage forms for venetoclax (for days 1-28 of the cycle). Alternatively, all three therapeutic agents could be included in one solid oral dosage form or each therapeutic agent could be present its separate solid oral dosage form. In some embodiments, a kit may include 5 solid oral dosage forms comprising cedazuridine, decitabine, and venetoclax (for days 1-5 of the cycle) and solid oral dosage forms (e.g., 23 solid oral dosage forms) of venetoclax for the remainder of the cycle (e.g., for days 6-28 of the cycle). In some embodiments, the unit dosage form for one therapeutic agent may vary within the kit. For example, in some embodiments, a kit may include for day one of the cycle a unit dosage form of 100 mg of venetoclax, and for another day of the cycle, a unit dosage form that includes 400 mg of venetoclax.

The kit may further comprise a container and/or a package suitable for commercial sale. The container can be in any conventional shape or form known in the art which is made of a pharmaceutically acceptable material, such as a paper or cardboard box, a glass or plastic bottle or jar, a re-sealable bag, or a blister pack with individual dosages for pressing out of the pack according to a therapeutic schedule. More than one container can be used together in a single package. For example, tablets may be contained in a blister pack which is in turn contained within a box. In some embodiments, the container is a bottle, e.g., a 30-cc white high-density polyethylene bottle containing unit dosage forms (e.g., about 5 unit dosage forms). The bottle may further contain desiccant, e.g., silica desiccant canisters. In some embodiments, the container is a blister pack, e.g., formed by aluminum foil or foil lidding containing one tablet per cavity. The blister packs may be present in a carton.

The kit may further comprise information. The information may be provided on a readable medium. The readable medium may comprise a label. The information may be directed towards a physician, pharmacist, or patient. The information may indicate that the unit dosage form may cause one or more adverse effects. The information may comprise instructions for administering the unit dosage form, such as in a manner described herein. These instructions may be provided in a variety of ways.

The information can be associated with the container, for example, by being: written on a label (e.g., the prescription label or a separate label) adhesively affixed to a container; included inside a container as a written package insert; applied directly to the container such as being printed on the wall of a box or blister pack; or attached as by being tied or taped, for example as an instructional card affixed to the neck of a bottle via a string, cord or other line, lanyard or tether type device.

Provided according to embodiments of the invention are methods of administering to a subject cedazuridine, decitabine, and venetoclax in one or more oral dosage forms of the invention. In particular embodiments, provided are methods of administering to a subject an oral dosage form comprising cedazuridine (e.g., 100 mg) and decitabine (e.g., 35 mg) and a pharmaceutically acceptable excipient and one or more oral dosage forms comprising venetoclax (e.g., totaling 100, 200, or 400 mg) and a pharmaceutically acceptable excipient. In some embodiments, each oral dosage form is a solid oral dosage form. The oral dosage form used may be any solid oral dosage form described herein.

Any administration regimen known to those skilled in the art for regulating the timing and sequence of drug delivery can be used and repeated as necessary to effect treatment in the methods of the invention. For example, the oral dosage forms of the invention may be administered 1, 2, 3 or 4 times daily, by a single dose, multiple discrete doses or continuous infusion. In particular embodiments, at least one solid oral dosage form is administered once daily. In some embodiments, the administering of at least one solid oral dosage form according to an embodiment of the invention may be performed for one or more weeks per 28-day cycle, e.g., one week, two weeks, three weeks, or four weeks per 28-day cycle. The weeks may be consecutive and/or non-consecutive. In particular embodiments, cedazuridine and decitabine are administered daily for 5 days (days 1-5) of the 28-day cycle and venetoclax is administered daily each day of the 28-day cycle.

In some embodiments of the invention, a solid oral dosage form comprising cedazuridine and decitabine is administered to a subject once daily for 1, 2, 3, 4, 5, 6, 7, 8, 9, 10, 11, 12, 13, 14, 15, 16, 17, 18, 19, 20, 21, 22, 23, 24, 25, 26, 27, 28, or more days. In some embodiments, a solid oral dosage form comprising cedazuridine and decitabine is administered to a subject once daily for days 1-5 of a 28-day cycle. In some embodiments, a second solid oral dosage form comprising venetoclax is administered to the same subject daily on the 1, 2, 3, 4, 5, 6, 7, 8, 9, 10, 11, 12, 13, 14, 15, 16, 17, 18, 19, 20, 21, 22, 23, 24, 25, 26, 27, 28, or more days. In some embodiments, on days 1-5 of a cycle, cedazuridine, decitabine, and venetoclax are each administered to the subject daily and on days 6-28 of the cycle, only venetoclax is administered daily. Such solid oral dosage forms may be administered concurrently (also referred to as simultaneously), sequentially, or at different times during the same day (also referred to as separately). In particular embodiments, all solid oral dosage forms are administered concurrently or at approximately the same time (e.g., within 5, 10, 15, 20, 25, or 30 minutes).

In some embodiments, a single unit dosage form comprising 35 mg decitabine and 100 mg cedazuridine may be administered daily on each of days 1-5 in the cycle. In some embodiments, the dosage for the venetoclax may vary with the day in the cycle. For example, on day 1, the subject may be administered 100 mg venetoclax (e.g., as a single 100 mg unit dosage form), on day 2, the subject may be administered 200 mg venetoclax (e.g., as two 100 mg unit dosage forms), and on days 3-28, the subject may be administered 400 mg of venetoclax (e.g., as four 100 mg unit dosage forms). However, in some embodiments, the doses of cedazuridine and decitabine may be varied, and in some embodiments, the doses of venetoclax may be the same for the entire cycle. As an example, in some embodiments of the invention, the subject may be administered 400 mg of venetoclax daily for each day in the cycle. This may be appropriate, for example, when it is a second or later cycle for the subject. More information regarding possible dosing schedules and administration for cedazuridine and decitabine may be found in the Inqovi® prescribing information and at www.inqovi.com.

In some embodiments, a time period of 0 to 31 days or more (e.g., 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 days or more) may pass between multiple cycles of the present invention. The time period of no treatment may be desirable to allow a subject (e.g., a human patient) of the present invention to have adequate health to continue treatment. The time period between treatment cycles can be determined by a physician using standard techniques in the art and may be determined individually on a per-subject basis, for example, as based on adequate blood count, e.g., adequate lack of neutropenia (e.g., absolute neutrophil count (ANC) in the subject of at least or greater than $0.5\times10^9$ cells/L) and may be adjusted over the course of treatment based on the judgement of the administering physician. In some embodiments, the time period between treatment cycles may be minimal, e.g., no time period, e.g., immediately starting on the next 28-day time period. In some embodiments, the time period between treatment cycles may be 1, 2, 3, 4, 5, or 6 days, or 1 week, 2 weeks, 3 weeks, 4 weeks, 5 weeks, 6 weeks, or more.

In some embodiments, the administration regimen may include pretreatment and/or co-administration with at least one additional therapeutic agent. In such case, the solid oral dosage form comprising decitabine and cedazuridine may be administered with the at least one additional therapeutic agent concurrently, sequentially, or at different times during the same or different day. The additional therapeutic agent may also be included within the one or more solid oral dosage forms. As used herein, the term "therapeutic agent" includes immunomodulatory agents.

Examples of chemotherapeutic agents include without limitation: alkylating agents (e.g., which may include doxorubicin, cyclophosphamide, estramustine, carmustine, mitomycin, bleomycin and the like); antimetabolites (e.g., which may include 5-Fluoro-Uracil, capecitabine, gemcitabine, nelarabine, fludarabine, methotrexate and the like); platinating agents (e.g., which may include cisplatin, oxaliplatin, carboplatin and the like); topoisomerase inhibitors (e.g., which may include topotecan, irinotecan, etoposide and the like); tubulin agents (e.g., which may include paclitaxel, docetaxel, vinorelbine, vinblastine, vincristine, other taxanes, epothilones, and the like); signaling inhibitors (e.g., kinase inhibitors, antibodies, farnesyltransferase inhibitors, and the like); and other chemotherapeutic agents (e.g., tamoxifen, anti-mitotic agents such as polo-like kinase inhibitors or aurora kinase inhibitors, and the like).

Furthermore, provided are methods of treating a disorder that is treatable with decitabine, venetoclax, and/or cedazuridine, in a subject in need thereof, comprising administering to the subject one or more oral dosage forms according to an embodiment of the invention, thereby treating the disorder in the subject. Any of the administration methods described herein may be used for treating the disorder or for any other therapeutic methods described herein.

In some embodiments of the invention, the disorder that is treatable with decitabine, venetoclax, and/or cedazuridine is a hyperproliferative disorder, e.g., cancer. The methods can be used to treat any cancer for which decitabine, venetoclax, and/or cedazuridine are known or later discovered to be effective in treating. In particular embodiments, the disorder is a cancer selected from hematological cancers and solid cancers. Examples of hematological cancers includes myelodysplastic syndromes (MDS), leukemia (e.g., ALL, AML, CML, MPN, or CMML), lymphoma (e.g., Hodgkin's Lymphoma, Non-Hodgkin lymphoma, or T-cell lymphoma), and plasma cell dyscrasias (e.g., multiple myeloma). In some embodiments, the solid cancer includes pancreatic cancer, ovarian cancer, peritoneal cancer, non-small cell lung cancer, breast cancer, neuroectodermal tumors and/or sarcomas. In some embodiments, the present invention provides a method for treating a hyperproliferative disorder, e.g., cancer, wherein the cancer is acute myeloid leukemia (ANIL).

The administering to a subject in need thereof of one or more solid oral dosage forms of the invention, or any combination of decitabine, venetoclax, and/or cedazuridine, may provide multiple beneficial responses to the subject. For example, in some embodiments, the administering reduces DNA methylation in the subject by at least 5% (e.g., at least 5, 6, 7, 8, 9, 10, 11, 12, 13, 14, or 15% or more or any value or range therein) as compared to a control measurement, e.g., as compared to DNA methylation in the subject prior to the administering (e.g., subject "baseline" DNA methylation). DNA methylation in the subject may be quantitatively and/or qualitatively evaluated by any standard technique in the art, e.g., as measured by a marker of relative global methylation as compared to a control, e.g., as measured by Long interspersed element-1 (LINE-1) methylation as compared to a control. For example, in some embodiments, the administering reduces LINE-1 methylation in the subject by at least 5% (e.g., at least 5, 6, 7, 8, 9, 10, 11, 12, 13, 14, or 15% or more) as compared to a control measurement, e.g., as compared to LINE-1 methylation in the subject prior to the administering (e.g., subject baseline LINE-1 methylation). For example, in some embodiments, the administering may reduce LINE-1 methylation in the subject by at least 5%, at least 8%, at least 10% or at least 15% or more. In some embodiments, the administering may reduce LINE-1 methylation in the subject by about 5% to about 20%, about 6% to about 15%, or by about 8% to about 10%.

In some embodiments, the administering may reduce absolute neutrophil count (ANC) in the subject to less than $0.5\times10^9$ cells/L of blood for no more than two, three, or four weeks (e.g., no more than 28, 27, 26, 25, 24, 23, 22, 21, 20, 19, 18, 17, 16, 15, 14, 13, 12, 11, 10, 9, 8, 7, 6, 5, 4, 3, 2, or 1 consecutive days or any value or range therein) following a 28-day cycle. In some embodiments, the administering reduces absolute neutrophil count (ANC) in the subject to less than $0.5\times10^9$ cells/L of blood for no more than two, three, or four weeks during treatment (e.g., between multiple, repeated 28-day cycles).

In some embodiments, the administering expands hemoglobin F-expressing cells (i.e., F cells) by at least 5% (e.g., at least 5, 6, 7, 8, 9, 10, 15, 20, 25, or 30% or more), optionally as measured by % F cells/erythrocytes per sample (e.g., in a patient blood sample) as compared to a "baseline" control % F cells/erythrocytes (e.g., as compared to % F cells/erythrocytes of the patient prior to treatment, e.g., as compared to the average % F cells/erythrocytes of a patient population not undergoing treatment (e.g., a healthy patient population)). For example, in some embodiments, the administering may expand % F cells in the subject by at least 5%, at least 8%, at least 10%, at least 15%, or at least 23% or more as compared to a baseline control. In some embodiments, the administering may expand % F cells in the subject by about 5% to about 30%, about 6% to about 24%, or by about 8% to about 20% as compared to a baseline control.

In some embodiments, the administering expands F cells to a total amount of at least 10% to at least 30% or more of total erythrocytes (e.g., at least 15%, 16%, 17%, 18%, 19%, 20%, 21%, 22%, 23%, 24%, 25%, 26%, 27%, 28%, 29%, or 30% or more F cells/erythrocytes or any value or range therein) per sample (e.g., in a patient blood sample). For example, in some embodiments, the administering may expand F cells to a total amount of at least 15%, at least 20%, at least 23%, at least 35% or more of total erythrocytes in a sample. In some embodiments, the administering may expand F cells to a total amount of about 15% to about 30%, about 18% to about 25%, or about 15% to about 35%, of total erythrocytes in a sample.

In some embodiments of the methods of the present invention, the subject may be a mammal. In some embodiments of the methods of the present invention, the subject may be a human. In some embodiments of the invention, the subject is aged 75 years or older. In particular embodiments, the subject is aged 18 years or older and ineligible for induction chemotherapy due to one or more comorbidities. Such comorbidities include, for example, (i) a baseline Eastern Cooperative Oncology Group (ECOG) performance status of 2 or 3, (ii) severe cardiac disorder (e.g., congestive heart failure requiring treatment, ejection fraction less than or equal to 50%, or chronic stable angina), (iii) severe pulmonary disorder (e.g., diffusing lung capacity for carbon monoxide DLCO less than or equal to 65% or forced expiratory volume in 1 second (FEV1) of less than or equal to 65%, (iv) creatinine clearance greater than or equal to 30 mL/min and less than 45 mL/min, and/or (v) moderate hepatic impairment with total bilirubin greater than 1.5 and less than or equal to 3.0× the upper limit of normal (ULN).

Dose levels, mode of administration, and administration regimen may be modified by those skilled in the art using known techniques as judged necessary for the subject (e.g., the patient).

It will be apparent to those skilled in the art that specific embodiments of the present invention may be directed to one, some or all of the above-indicated aspects as well as other aspects, and may encompass one, some or all of the above- and below-indicated embodiments, as well as other embodiments.

Other than in the working examples, or where otherwise indicated, all numbers expressing quantities of ingredients, reaction conditions, and so forth used in the specification and claims are to be understood as being modified by the term "about". Accordingly, unless indicated to the contrary, such numbers are approximations that may vary depending upon the-desired properties sought to be obtained by the present invention. At the very least, and not as an attempt to limit the application of the doctrine of equivalents to the scope of the claims, each numerical parameter should be construed in light of the number of significant digits and ordinary rounding techniques.

While the numerical ranges and parameters setting forth the broad scope of the invention are approximations, the numerical values set forth in the working examples are reported as precisely as possible. Any numerical value, however, inherently contains certain errors necessarily resulting from the standard deviation found in their respective testing measurements.

Having described the present invention, the same will be explained in greater detail in the following examples, which are included herein for illustration purposes only, and which are not intended to be limiting to the invention.

EXAMPLE

A single-arm, open-label, multicenter, non-randomized interventional study is being performed to evaluate the pharmacokinetic (PK) interaction, safety, and the preliminary efficacy of ASTX727 (cedazuridine in combination with decitabine) when given in combination with venetoclax for the treatment of newly diagnosed acute myeloid leukemia (AML) in adults who are age 75 years or older and/or have comorbidities that preclude the use of intensive induction chemotherapy. The study will evaluate any drug-drug interactions between ASTX727 and venetoclax combination therapy by evaluating the area under the curve (AUC) and maximum plasma concentration (Cmax) exposure. 35 participants are estimated to be enrolled in a single group assignment intervention model with treatment being the primary purpose.

Dosing Regimen: Oral Administration of ASTX727 and Venetoclax Combination

Cycle 1: ASTX727 administered according to the prescribed dosing regimen in combination with venetoclax (day 1=administration of 100 mg daily; day 2=administration of 200 mg daily; and days 3-28=administration of 400 mg daily) for a 28-day cycle.

Cycle 2 and beyond: ASTX727 administered according to the prescribed dosing regimen in combination with venetoclax (400 mg daily) for a 28-day cycle.

Results to be Measured

Primary Outcome Measures

Venetoclax $AUC_{0-24}$—on days 5 and 15 in Cycle 2 (28 days per cycle) measure venetoclax area under the curve (AUC) from time 0 to 24 hours with and without ASTX727.

Venetoclax Cmax—on days 5 and 15 in Cycle 2 (28 days per cycle), measure venetoclax maximum observed concentration with and without ASTX727.

Secondary Outcome Measures

Decitabine $AUC_{0-24}$—on days 1, 2, and 5 in Cycle 2 (28 days per cycle), measure decitabine area under the curve from time 0 to 24 hours.

Decitabine and Cedazuridine Cmax—on days 1, 2, and 5 in Cycle 2 (28 days per cycle), measure decitabine and cedazuridine maximum observed concentrations.

Cedazuridine $AUC_{0-8}$—on days 1, 2, and 5 in Cycle 2 (28 days per cycle) measure cedazuridine area under the curve from time 0 to 8 hours.

Decitabine 5-day AUC—on days 1 to 5 in Cycle 2 (28 days per cycle) measure decitabine 5-day cumulative AUC.

Participants with TEAEs—up to 24 months, measure the number of treatment-emergent adverse events (TEAEs).

Complete response (CR)—up to 24 months, measure the number of participants with CR, CR+ complete response with partial hematological recovery (CRh), and CR+ incomplete blood count recovery (CRi).

Time to Response—up to 24 months, measure the number of days from the first dose to the first documented evidence of complete response or CRh.

Duration of Response—up to 24 months, measure number of days from the start of response (CR or CRh) until disease progression, start of alternative antileukemia therapy, or death.

Overall response—up to 24 months, measure number of days from date of first dose until death due to any cause.

Eligibility Criteria

Ages Eligible for Study: 18 years or older

Sexes Eligible for Study: All

Gender Based: No

Accepts Healthy Volunteers: No

Inclusion Criteria

Participant must be 18 years or older.

Histological confirmation of newly diagnosed AML by the World Health Organization (WHO) 2016 criteria.

Projected life expectancy of at least 3 months.

Participants must be considered ineligible for intensive induction chemotherapy defined by the following: a) Aged 75 year or older, or b) Aged 18-74 with at least one of the following comorbidities: (i) severe cardiac disorder (e.g., congestive heart failure requiring treatment, ejection fraction less than or equal to 50%, or chronic stable angina), (ii) severe pulmonary disorder (e.g., diffusing lung capacity for carbon monoxide DLCO less than or equal to 65% or forced expiratory volume in 1 second (FEV1) of less than or equal to 65%, (iii) creatinine clearance greater than or equal to 30 mL/min and less than 45 mL/min, and (iv) moderate hepatic impairment with total bilirubin greater than 1.5 and less than or equal to 3.0× the upper limit of normal (ULN).

Eastern Cooperative Oncology Group (ECOG) Performance Status of 0-2.

Women of child-bearing potential (according to the recommendations of the Clinical Trial Facilitation Group (CTFG)) must not be pregnant or breastfeeding and must have a negative pregnancy at screening.

Participants and their partners with reproductive potential must agree to use at least 2 effective contraceptive measures during the study and for 3 months after the last dose of the study treatment, including refraining from sperm donation. Effective contraception includes methods such as oral contraceptives or double-barrier method (e.g., use of condom and diaphragm, with spermicide).

Capable of giving signed informed consent, which includes compliance with the requirements and restrictions listed in the informed consent form and protocol, and willing to participate in the study.

Exclusion Criteria

History of myeloproliferative neoplasm including myelofibrosis, essential thrombocythemia, polycythemia vera, chronic myeloid leukemia with or without BCR-ABL1 translocation and AML with BCR-ABL1 translocation.

The following karyotype abnormalities t(8;21), inv(16), t(15;17), or other acute promyelocytic leukemia variants that remain sensitive to all-trans retinoic acid (ATRA) therapy.

Known active central nervous system involvement from AML.

Known human immunodeficiency virus (HIV) infection (due to potential drug-drug interactions between antiretroviral medications and venetoclax). HIV testing will be performed at screening, only if indicated per local guidelines or institutional standards.

Known active hepatitis B or C infection (detectable viral load). Hepatitis B or C testing will be performed at screening, only if indicated per local guidelines or institutional standards.

Severe hepatic impairment defined as: bilirubin>1.5× ULN for participants≥75 years or >3×ULN for participants <75 years; or aspartate aminotransferase (AST)/serum glutamic oxaloacetic transaminase (SGOT) or alanine aminotransferase (ALT)/serum glutamic pyruvic transaminase (SGPT)>3×ULN (unless considered to be due to leukemic organ involvement).

Severe renal impairment defined as: calculated creatinine clearance or glomerular filtration rate<30 mL/min.

A malabsorption syndrome or other condition that precludes enteral route of administration.

Cardiovascular disability status of New York Heart Association Class>2. Class 2 is defined as cardiac disease in which patients are comfortable at rest but ordinary physical activity results in fatigue, palpitations, dyspnea, or anginal pain.

Chronic respiratory disease that requires continuous oxygen, or significant history of renal, neurologic, psychiatric, endocrinologic, metabolic, immunologic, hepatic, cardiovascular disease, any other medical condition or known hypersensitivity to any of the study medications that in the opinion of the investigator would adversely affect his/her participating in this study.

Clinically significant uncontrolled systemic infection requiring therapy (viral, bacterial, or fungal).

History of other malignancies prior to study entry, with the exception of adequately treated in situ carcinoma of the breast or cervix uteri; localized basal cell carcinoma or squamous cell carcinoma of the skin; previous malignancy confined and surgically resected (or adequately treated and controlled with other modalities); and any early-stage malignancy for which no definitive therapy is required.

White blood cell (WBC) count>25,000/μL (hydroxyurea treatment is permitted to meet this criterion).

Treatment with the following: a) a hypomethylating agent (azacitidine or decitabine), or venetoclax including prior treatment for myelodysplastic syndrome (MDS), b) Chimeric Antigen Receptor (CAR)-T cell therapy, c) investigational therapeutic agents for MDS or AML.

Participants who cannot discontinue concomitant prophylactic antifungal therapy with CYP3A inhibitor activity or other concomitant medications with moderate or strong CYP3A inhibitor activity≥7 days or 5 half-lives, whichever is greater, prior to cycle 1 day 1 (C1D1).

Participants who cannot discontinue concomitant drugs that are strong CYP3A or P-gp inhibitors ≥7 days or 5 half-lives, whichever is greater, prior to C1D1.

Participants who cannot avoid concomitant drugs known as moderate or strong CYP3A inducers.

Current participation in another research or observational study.

Known or suspected hypersensitive to decitabine, cedazuridine, venetoclax, or any of their excipients.

Known significant mental illness or other condition such as active alcohol or other substance abuse or addiction that, in the opinion of the investigator, predisposes the participant to high risk of noncompliance with the protocol.

Patients who consume grapefruit, grapefruit products, Seville oranges (including marmalade containing Seville oranges) or starfruit≤7 days prior to C1D1.

The foregoing examples are illustrative of the present invention, and are not to be construed as limiting thereof. Although the invention has been described in detail with reference to preferred embodiments, variations and modifications exist within the scope and spirit of the invention as described and defined in the following claims.

What is claimed is:

1. A method of treating cancer selected from hematological cancers and solid cancers in a subject in need thereof, comprising administering to the subject an effective amount of cedazuridine, an effective amount of decitabine, and an effective amount of venetoclax, wherein the effective amount of cedazuridine, the effective amount of decitabine, and the effective amount of venetoclax are each administered as an oral dosage form, thereby treating the cancer in the subject.

2. The method of claim 1, wherein the hematological cancer is selected from at least one of myelodysplastic syndromes (MDS), myeloproliferative neoplasms (MPN), leukemia, and lymphoma.

3. The method of claim 2, wherein the leukemia is ALL, AML, CML, MPN, or CMML.

4. The method of claim 3, wherein the leukemia is AML.

5. The method of claim 1, wherein the subject is aged 75 years or older.

6. The method of claim 1, wherein the subject has comorbidities that preclude the use of standard induction chemotherapy.

7. The method of claim 1, wherein the effective amount of cedazuridine, the effective amount of decitabine, and the effective amount of venetoclax are administered simultaneously, sequentially, or separately.

8. The method of claim 1, wherein each oral dosage form is a solid oral dosage form.

9. The method of claim 8, wherein the effective amount of cedazuridine and the effective amount of decitabine are administered together in a combination solid oral dosage form.

10. The method of claim 1, wherein the effective amount of cedazuridine and the effective amount of decitabine are administered on days 1-5 of a 28-day cycle, and the effective amount of venetoclax is administered each day of the 28-day cycle.

11. The method of claim 1, wherein the effective amount of cedazuridine and the effective amount of the decitabine are present in a first solid oral dosage form that comprises 100 mg cedazuridine, 35 mg decitabine, and at least one pharmaceutically acceptable excipient, and wherein the effective amount of venetoclax is present in at least one second solid oral dosage form that comprises 50 mg or 100 mg of venetoclax and at least one pharmaceutically acceptable excipient.

12. The method of claim 1, wherein the subject is administered an effective amount of cedazuridine, an effective amount of decitabine, and 100 mg of venetoclax on day 1 of a cycle; an effective amount of cedazuridine, an effective amount of decitabine, and 200 mg of venetoclax on day 2 of the cycle; an effective amount of cedazuridine, an effective amount of decitabine, and 400 mg of venetoclax on days 3-5 of the cycle; and 400 mg of venetoclax on days 6-28 of the cycle.

13. The method of claim 1, wherein the subject is administered an effective amount of cedazuridine, an effective amount of decitabine, and 400 mg of venetoclax on days 1-5 of a cycle, and 400 mg of venetoclax on days 6-28 of the cycle.

14. An oral dosage form comprising cedazuridine, decitabine, and venetoclax, and at least one pharmaceutically acceptable excipient.

15. The oral dosage form of claim 14, wherein the oral dosage form is a solid oral dosage form.

16. The method of claim 6, wherein the comorbidities are one or more selected from the group consisting of (i) severe cardiac disorder, (ii) severe pulmonary disorder, (iii) creatinine clearance greater than or equal to 30 mL/min and less than 45 mL/min, and (iv) moderate hepatic impairment with total bilirubin greater than 1.5 and less than or equal to 3.0× the upper limit of normal (ULN).

* * * * *